United States Patent
Rudolecky et al.

(10) Patent No.: US 10,240,549 B2
(45) Date of Patent: Mar. 26, 2019

(54) SYSTEM AND METHOD FOR EVALUATING CHIP ZAP DATA

(71) Applicant: HONEYWELL INTERNATIONAL INC., Morris Plains, NJ (US)

(72) Inventors: Tomas Rudolecky, Brno (CZ); Chris Hickenbottom, Phoenix, AZ (US); Zdenek Hrncir, Brno (CZ); Onder Uluyol, Fridley, MN (US); Kyusung Kim, Plymouth, MN (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 72 days.

(21) Appl. No.: 15/398,278

(22) Filed: Jan. 4, 2017

(65) Prior Publication Data
US 2018/0187622 A1 Jul. 5, 2018

(51) Int. Cl.
*F02D 41/22* (2006.01)
*F01M 11/10* (2006.01)
*G01N 33/28* (2006.01)

(52) U.S. Cl.
CPC ............ *F02D 41/22* (2013.01); *F01M 11/10* (2013.01); *G01N 33/2888* (2013.01); *F01M 2011/1466* (2013.01); *F02D 2041/228* (2013.01)

(58) Field of Classification Search
CPC ....... F02D 41/22; F02D 41/228; F01M 11/10; F01M 2011/1466; G01N 33/2888
USPC ....................................................... 701/29.5
See application file for complete search history.

(56) References Cited

U.S. PATENT DOCUMENTS

| | | | |
|---|---|---|---|
| 4,219,805 A | 8/1980 | Magee et al. | |
| 5,406,208 A | 4/1995 | Bitts | |
| 6,917,865 B2 * | 7/2005 | Arai | F01M 11/10 340/450.3 |
| 7,581,434 B1 * | 9/2009 | Discenzo | G01N 33/2888 73/53.01 |
| 9,068,520 B2 * | 6/2015 | Masuda | F02D 29/02 |
| 9,205,845 B2 | 12/2015 | Uluyol et al. | |
| 9,404,403 B2 * | 8/2016 | McDonald | F01M 11/12 |
| 2007/0156312 A1 * | 7/2007 | Breed | B60C 23/007 701/31.4 |
| 2013/0158838 A1 * | 6/2013 | Yorke | B60W 10/06 701/103 |
| 2014/0121994 A1 | 5/2014 | Jean et al. | |

(Continued)

FOREIGN PATENT DOCUMENTS

WO 9303458 A1 2/1993

OTHER PUBLICATIONS

Miller, J.L. et al.; In-Line Oil Debris Monitor for Aircraft Engine Condition Assessment; Pratt & Whitney Aircraft Co., East Hartford, CT and Gas TOPS Ltd, Ottawa, ON Canada; IEEE.

(Continued)

*Primary Examiner* — Atul Trivedi
(74) *Attorney, Agent, or Firm* — Lorenz & Kopf, LLP (57) ABSTRACT

A system and method for identifying engine wear based on engine oil debris is provided. The provided system and method utilize metallic debris data provided in summary reports. For each object of metallic debris, a zap count, an initial (pre-zap) impedance and an impedance change (post zap) are processed with configurable reference variables. Alerts (suggesting potential engine wear) are generated responsive to the impedance values of the objects of metallic debris and the reference variables.

16 Claims, 4 Drawing Sheets

(56) References Cited

U.S. PATENT DOCUMENTS

| | | | |
|---|---|---|---|
| 2015/0176558 A1* | 6/2015 | Glugla | F02P 17/12 |
| | | | 123/294 |
| 2016/0195509 A1* | 7/2016 | Jamieson | G01N 33/2858 |
| | | | 356/70 |
| 2017/0081997 A1* | 3/2017 | Potyrailo | G01N 33/2888 |
| 2017/0241360 A1* | 8/2017 | Ohsaki | G07C 5/00 |
| 2018/0068497 A1* | 3/2018 | Kurtz | F02D 41/021 |
| 2018/0204393 A1* | 7/2018 | Landolsi | B60L 11/1851 |

OTHER PUBLICATIONS

"Smart Zapper System", located at http ://www.eaton.com/ecm/groupsl/public/@pub/@eaton/@aero/documents/content/ct_194547.pdf. Document published Oct. 2013 by Eaton Aerospace Group.
Great Britain Combined Search and Examination Report under Sections 17 and 18(3) for Application GB1800077.8 dated Jun. 18, 2018.

* cited by examiner

FIG. 1

| Engine Chip Summary | | | | | |
|---|---|---|---|---|---|
| Date | Time | Imp 0 | Imp 1 | Imp Diff | Zaps |
| 10-18-15 | 19:06:48 | 232.11 | 1886.23 ohms | 1654.12 ohms | 1 |
| 10-12-15 | 22:05:54 | 11.62 | 1782.64 ohms | 1771.02 ohms | 1 |
| 10-12-15 | 19:24:21 | 261.73 | 1885.71 ohms | 1623.99 ohms | 1 |
| 10-11-15 | 20:39:24 | 227.32 | 1875.04 ohms | 1647.72 ohms | 1 |
| 10-11-15 | 19:10:02 | 169.89 | 1849.58 ohms | 1679.69 ohms | 1 |
| 10-05-15 | 13:10:37 | 7.77 | 1781.06 ohms | 1773.29 ohms | 1 |
| 10-04-15 | 03:24:51 | 158.05 | 1842.36 ohms | 1684.32 ohms | 1 |
| 10-01-15 | 15:07:37 | 29.00 | 2891.18 ohms | 2862.18 ohms | 1 |
| 09-25-15 | 21:38:44 | 164.30 | 1844.86 ohms | 1680.55 ohms | 1 |

SYSTEM AND METHOD FOR EVALUATING CHIP ZAP DATA

TECHNICAL FIELD

The present invention generally relates to engine diagnostics, and more particularly relates to a system and method for evaluating potential engine wear based on engine oil debris.

BACKGROUND

Various inspections and diagnostics are employed to monitor wear and tear on an engine. With respect to metallic components within an engine (for example, engine bearings, the aft sump pump, and the gearbox), wear and tear may manifest as the flaking off of metallic debris into an oil subsystem used for lubricating the engine. Therefore, evaluating the oil associated with an engine is one diagnostic approach employed in engine health monitoring systems.

In some approaches to evaluating engine oil, a metallic chip detector collects ferrous metals from scavenged engine oil returned to the oil tank; in this approach the metallic chip detector may include magnets. In other approaches, a metallic chip detector evaluates the scavenged oil for both ferrous and nonferrous metallic debris by determining, for each object of metallic debris, a measure of initial impedance across a gap, as the measure of impedance provides conductivity information. In these approaches, when an object of metallic debris is detected, it is often "zapped" with a high energy electrical charge that is intended to burn/eliminate the metallic debris. This procedure is referred to as "chip zap." Often, a number of repetitions of zapping may be employed in effort to eliminate each object of metallic debris detected, and this number, along with the initial impedance of the metallic debris, is recorded as chip zap data into a summary report.

The summary reports are often stored and evaluated later. When the summary reports are associated with a turbofan engine of an aircraft, the evaluation of the summary report generally occurs as part of an engine health maintenance review at a ground station. A number of zaps in a summary report has been utilized to postulate that the engine has experienced enough wear and tear that it should be removed and replaced. However, subsequent engine analysis has indicated that this measure of wear and tear is somewhat inefficient, in that it results in removing and replacing more engines than necessary (often referred to as resulting in too many false positives). As is readily appreciated, replacement of an engine is costly and time consuming.

Therefore, an improved system and method for identifying engine wear based on engine oil debris is desirable. The desirable system and method utilize chip zap data provided in summary reports, and process, for each object of metallic debris, an initial (pre-zap) impedance and an impedance change (post zap) with respect to configurable reference variables. The desirable system and method generate alerts (suggesting potential engine wear) responsive to the impedance values of the objects of metallic debris and the reference variables. The provided system and method realize these improvements. Furthermore, other desirable features and characteristics of the exemplary embodiments will become apparent from the subsequent detailed description.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

Provided is a computer implemented method for automatically identifying engine wear based on engine oil debris. The method comprises: initializing reference variables comprising a threshold zap count and a delta time; initializing a zap counter to zero; receiving a line of a summary report associated with the engine oil debris; storing the line in a computer readable storage medium; processing the line to identify a date, an initial Z, a delta Z, and a number of zaps; incrementing the zap counter by the number of zaps, when the date is within a cutoff date; and generating an alert when the zap counter reaches the threshold zap count.

A system for automatically identifying engine wear based on engine oil debris is also provided. The system comprises: a processor; and a computer readable storage medium coupled to the processor; wherein the processor is configured to initialize reference variables comprising a threshold zap count and a cutoff date; initialize a zap counter to zero; receive a line of a summary report associated with the engine oil debris; store the line; process the line to identify a date and a number of zaps; when the date is within the cutoff date, increment the zap counter by the number of zaps; and generate an alert when the zap counter reaches the threshold zap count.

Another computer implemented method for automatically identifying engine wear based on engine oil debris is provided. The method comprises: initializing reference variables comprising a threshold zap count, a delta time, a threshold initial impedance (Z), a threshold delta Z, a low Z limit, and a delta Z limit; initializing a zap counter to zero, a low Z counter to zero, and a delta Z counter to zero; receiving a line of a summary report associated with the engine oil debris; storing the line in a memory device; processing the line to identify a date, an initial Z, a delta Z, and a number of zaps; processing the date and the delta time to create a cutoff date; incrementing the zap counter by the number of zaps; incrementing the low Z counter when the initial Z is lower than the threshold initial Z; incrementing the delta Z counter when the delta Z is greater than the threshold delta Z; and while there is a next line in the summary report, reading the next line in the summary report and storing it in a memory device; and processing the line to identify a date, an initial impedance, a delta impedance, and a number of zaps; and when the date is within the cutoff date, incrementing the zap counter by the number of zaps; incrementing the low Z counter when the initial Z is lower than the threshold initial Z; and incrementing the delta impedance counter when the delta impedance is greater than the threshold delta impedance; and selectively generating an alert upon the occurrence of any of the conditions (i) the zap counter reaches the threshold zap count, (ii) the low Z counter reaches the low Z limit, and (iii) the delta Z counter reaches the delta Z limit.

Furthermore, other desirable features and characteristics of the system and method will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention that is defined by the claims. Furthermore, there is no intention to be bound by any expressed or implied theory presented in the preceding technical field, background, brief summary, or the following detailed description.

As is known by persons of skill in the art, generally, a low impedance (low Z) implies an electrical coupling (i.e., conductance) and a high impedance (high Z) implies a lack of electrical coupling. The provided embodiments employ a selectively configurable threshold impedance (Z) variable to indicate whether a detected object of metallic debris is substantial enough to be counted as a measure of engine wear. The threshold Z is application specific and distinguishes between a low Z object of metallic debris (referred to herein as a metallic chip, of concern herein) and a high Z object of metallic debris (referred to herein as metallic fuzz). In this manner, the provided embodiments go beyond determining that metallic debris is present by additionally vetting the detected metallic debris. Vetting the metallic debris in this manner leads to fewer false positives, less replaced engines, and reduced cost.

Figure 1:
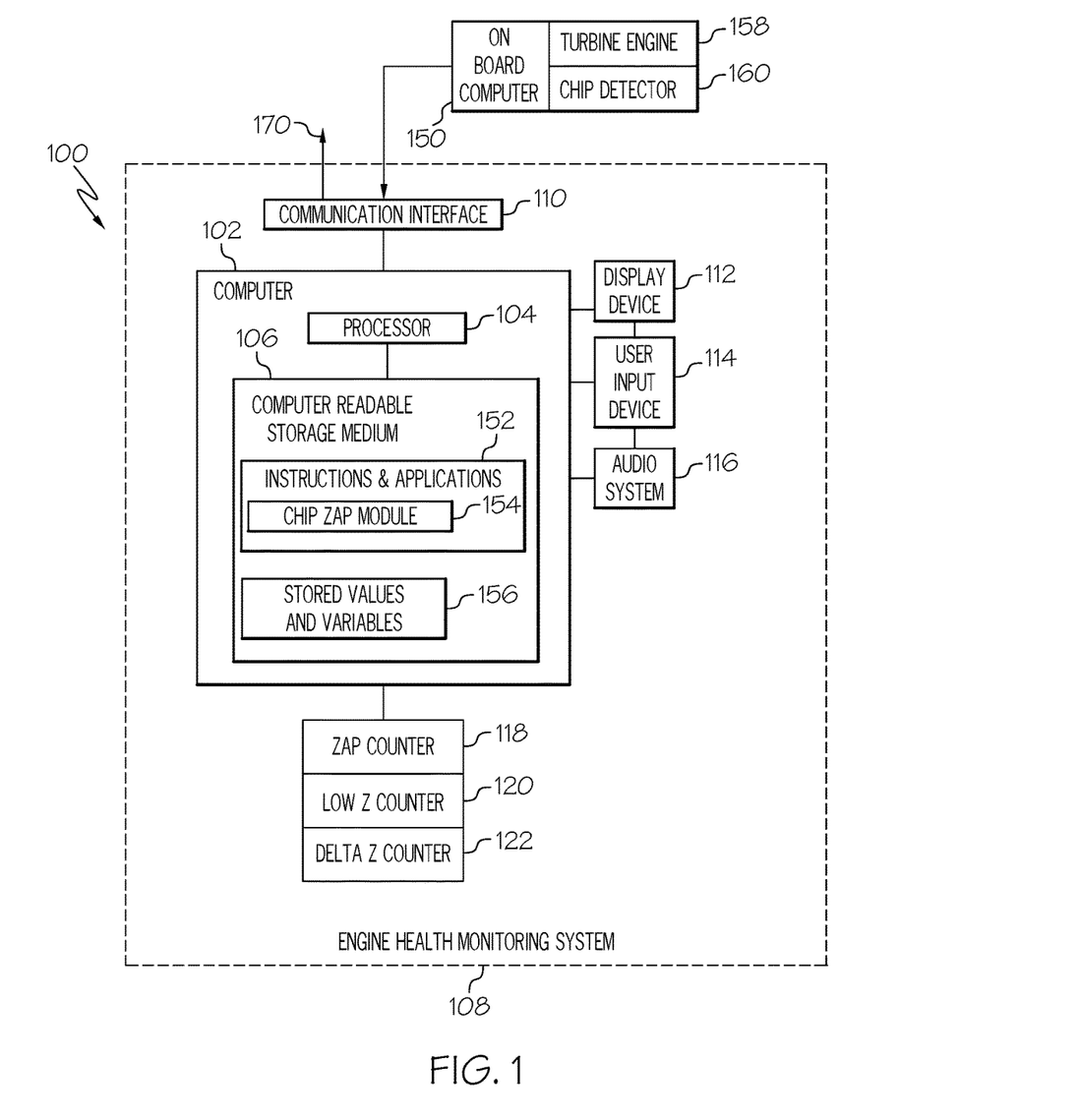
FIG. 1 is a functional block diagram of a system for automatically identifying engine wear based on engine oil debris, in accordance with exemplary embodiments.

Referring to FIG. 1, a functional diagram of a system 100 for automatically identifying engine wear based on engine oil debris is depicted, in accordance with various embodiments. The system 100 includes a computer 102 that may be an integral part of an engine health monitoring system 108, and configured for operable communication with components of the engine health monitoring system 108. Non-limiting examples of the components of the engine health monitoring system 108 include: a communication interface 110, a display device 112, a user input device 114, an audio system 116, a zap counter 118, a low impedance (Z) counter 120, and a delta impedance (Z) counter 122. One or more external sources 150 may be in operable communication with the computer 102, via the communication interface 110. In some embodiments, the external source 150 comprises an onboard computer coupled to a chip detector and a turbine engine (wherein onboard means onboard a mobile platform such as an aircraft). In some embodiments, the computer 102 is integrated with the counters (118, 120, and 122), for example, the processor 104 may maintain one or more of the counters (118, 120, and 122) within the computer readable storage medium 106. In some embodiments, the computer 102 is also integrated with the communication interface 110. These functional blocks are described in detail below.

The computer 102 includes at least one computer processor 104 that is in communication with a tangible, non-transitory computer-readable storage medium 106 by way of a communication bus or other such computing infrastructure. The processor 104 is illustrated in one block, but may include various different processors and/or integrated circuits that collectively implement any of the functionality described herein. The processor 104 includes a central processing unit (CPU) that is in communication with the computer readable storage medium 106. An I/O interface (not illustrated) may be any entry/exit device adapted to control and synchronize the flow of data into and out of the CPU from and to peripheral devices such as input/output devices used to interface with other functional blocks within the engine health monitoring system 108. In various embodiments, the computer 102 stores and retrieves data from the computer readable storage medium 106, commands the display device 112, the audio system 116, and/or generates soft files in the computer readable storage medium 106.

The computer readable storage medium 106 can include any known form of computer-usable or computer-readable (storage) medium. The computer-readable (storage) medium of computer readable storage medium 106 can be any type of memory technology including any types of read-only memory or random access memory or any combination thereof. This encompasses a wide variety of media that include, for example but not limited to, an electronic, magnetic, optical, electromagnetic, infrared, or semiconductor system, apparatus, device, or propagation medium. Some non-limiting examples include volatile media, non-volatile media, removable media, and non-removable media. The term computer-readable medium and variants thereof, as used in the specification and claims, refer to any known computer storage media. In some embodiments, storage media includes volatile and/or non-volatile, removable, and/or non-removable media. For example, storage media could include any of random-access memory (RAM), read-only memory (ROM), electrically erasable programmable read-only memory (EEPROM), solid state memory or other memory technology, CD ROM, DVD, other optical disk storage, magnetic tape, magnetic disk storage or other magnetic storage devices, and any other medium that can be used to store desired data. For sake of simplicity of illustration, the computer readable storage medium 106 is illustrated as a single block within computer 102; however, the computer readable storage medium 106 can be distributed throughout the engine health monitoring system 108, in any of the various blocks illustrated in FIG. 1, and can be implemented using any combination of fixed and/or removable storage devices depending on the implementation.

The computer readable storage medium 106 stores processor readable instructions 152. The processor readable instructions 152 can be distributed across or among one or more modules and applications stored in the computer readable storage medium 106. The processor readable instructions 152 may embody one or more programs or applications which can be loaded and executed by the processor 104. Within the processor readable instructions 152, the chip zap module 154 includes program code and pre-defined rules for relations among various pieces of information, rules, and algorithms sufficient to perform the functions of the system 100 as described herein. The computer readable storage medium 106 additionally comprises stored values and variables 156. In operation, performance of the steps of a method or process associated with the system 100 includes referencing stored values and variables 156 and executing the processor readable instructions embodied in the chip zap module 154. The processor 104 may store some or all of a summary report in the computer readable storage medium 106.

The user input device 114 may be any one, or combination, of various known user input device devices including, but not limited to, a touch sensitive screen, a cursor control device (CCD) (not shown), such as a mouse, a trackball, or joystick, and/or a keyboard, one or more buttons, switches, or knobs. In the depicted embodiment, the user input device 114 includes a CCD and a keyboard (not shown). A user provides input via the user input device 114. In some embodiments, the user input device 114 and display device 112 are integrated, such as in the case of a touch sensitive screen.

In various embodiments, the external source 150 is a mobile platform, such as an aircraft. Regardless of the form of the external source 150, it comprises an engine having an oil subsystem and a chip detector system sufficient to produce the summary reports of chip zap data for the engine as described hereinbelow. Accordingly, "data from the external source 150" comprises the summary reports for the engine. In an embodiment, the engine may be a gas turbine engine.

The computer 102, and processor 104, receives the data from external sources 150 via wireless or wired communication managed by the communication interface 110. In order to support wireless communication, by the communication interface 110 includes at least one receiver and at least one transmitter that are operatively coupled to at least one processor such as the processor 104. The communication interface 110 can enable the computer 102 to establish and maintain the communications links to one or more external sources 150. The communication interface 110 can perform signal processing (e.g., digitizing, data encoding, modulation, etc.) as is known in the art.

In various embodiments, the display device 112 and the audio system 116 are employed to alert and direct the attention of a user. The display device 112, in response to commands from the computer 102, selectively renders symbology, such as alphanumeric, graphic, and/or iconic information, thereby supplying visual feedback to a user. It will be appreciated that the display device 112 may be implemented using any one of numerous known display devices suitable for rendering textual, graphic, and/or iconic information in a format viewable by a user. Non-limiting examples of such display devices 112 include cathode ray tube (CRT) displays, and flat panel displays such as LCD (liquid crystal displays) and TFT (thin film transistor) displays. The display device 112 may be implemented as a panel mounted display, a computer monitor, or as any one of numerous known display technologies. The audio system 116 is also configured to receive commands and data from the computer 102, and to emit audible sounds and speech responsive thereto. In addition to displayed and annunciated alerts, the computer 102 may generate textual or alphanumeric alerts within a soft file that may be stored in the computer readable storage medium 106, printed, and/or transmitted externally, for example, in an email, via data output 170.

In operation, the processor 104 is configured to initialize reference variables and to initialize counters (118, 120, and 122). Reference variables are configurable and predetermined, and they include, but are not limited to, a threshold zap count, a delta time, a threshold initial impedance (threshold initial Z), a threshold delta impedance (threshold delta Z), a low Z limit, and a delta Z limit. The threshold initial Z is an impedance value set low enough to likely indicate a metallic object of concern. The threshold delta Z is an impedance value set large enough to likely represent, particularly when combined with the threshold initial Z, that an object of metallic debris has been cleared (reduced or eliminated) by the high energy zap of a chip detector system. In an embodiment, threshold initial Z is 20 ohms and threshold delta Z is 1700 ohms. The threshold zap count, low Z limit, and delta Z limit represent the number of times the associated event can happen before triggering an alert. For example, the threshold zap count is how many zaps can be tolerated by the system in a given amount of time; the low Z limit is the number of low impedance entries may be detected before generating an alert, and the delta Z limit is the number of entries having large swings in impedance change after a zap that may be tolerated by the system 100 before generating an alert. Initializing the reference variables, as used herein, includes retrieving the reference variables from the stored values and variables 156 in the computer readable storage medium 106, and may further include receiving the reference variables via the user input device 114 and storing them. Initializing the counters includes setting the zap counter 118 to zero, the low Z impedance counter 120 to zero, and the delta Z counter 122 to zero.

It should be understood that FIG. 1 is a simplified representation of a system 100 for purposes of explanation and ease of description, and FIG. 1 is not intended to limit the application or scope of the subject matter in any way. In practice, the system 100 and/or external source 150 will include numerous other devices and components for providing additional functions and features, as will be appreciated by those with skill in the art.

Summarizing FIG. 1, the processor 104 is configured to, responsive to engine oil data from the external source 150, process the data to make determinations about individual objects of metallic debris in the engine oil, and generate alerts based thereon. The processor 104 generates alerts when predetermined threshold values are violated, indicating potential engine wear. The processor 104 supplies appropriate commands to the display device 112 and/or audio system 116, such that alerts may be annunciated. This functionality is described in more detail below.

Figure 2:
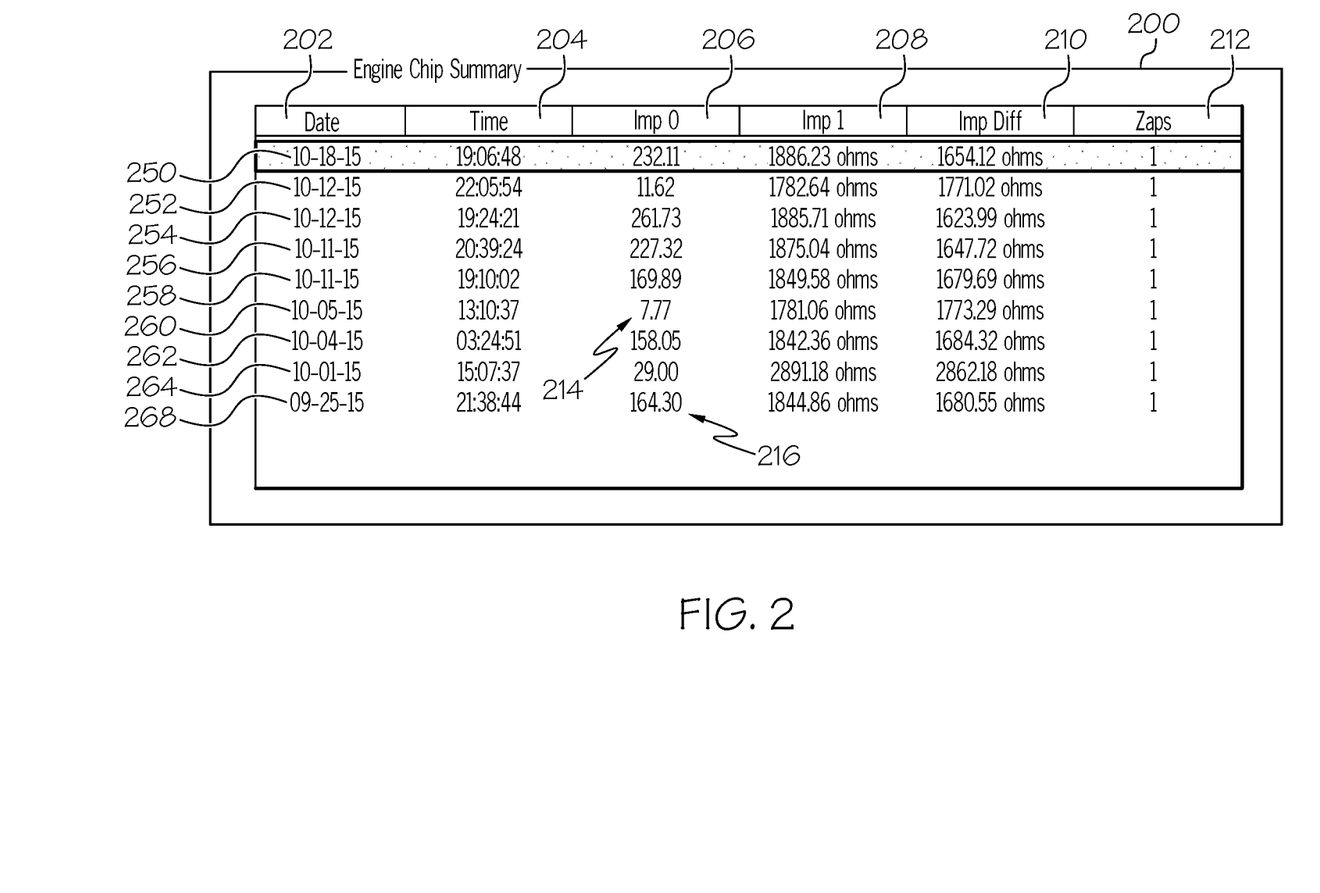
FIG. 2 is an example of a summary report for an engine, in accordance with an exemplary embodiment.

Turning now to FIG. 2, the summary report 200 is generated by the external source 150 comprising a chip detector 160 associated with an engine 158 for which the present system and method are to evaluate engine wear. In the embodiment depicted in FIG. 2, summary report 200 data is organized into data columns, which include, but are not limited to, a date 202, a time 204, an initial impedance 206 "imp 0" (pre-zap), a post-zap impedance 208 "imp 1", a delta impedance 210 "imp diff" (which is the difference between imp 0 (206) and imp 1 (208)), and a number of zaps 212. As may readily be appreciated, the data columns may be differently arranged, and the summary report 200 may include additional information, in additional columns. The summary report 200 is further comprised of one or more lines (250-266). The chip zap module 154 is understood to have the rules and instructions required for properly identifying the summary report 200, the data columns, and a number of lines (N) in the summary report 200.

As mentioned, the summary report 200 comprises information about objects of metallic debris in the engine oil associated with the engine 158. The provided system 100 and method (FIG. 3 300) determine whether a detected metallic object in the engine oil is a metallic chip of concern or metallic fuzz. Also previously mentioned, a metallic object is identified as a metallic chip when it is substantial enough to create an electrical coupling across a gap that should not be electrically coupled; metallic objects that are less substantial are identified as metallic fuzz. As may be appreciated, "substantial enough" is application specific, configurable, and determined by the threshold initial Z. For example, in FIG. 2, the value of 7.77, at arrow 214, is determined to indicate a metallic chip, whereas the value of 164.30, at arrow 216, is determined to indicate metallic fuzz. After a high energy electronic pulse is directed at the metallic object, it is desirable that the metallic object is eliminated or vaporized and the post zap Z is high.

Referring back to FIG. 1, the computer 102 receives the summary report 200 data from external source 150. The summary report 200 data may be received line by line, in chunks of lines, or as a completed summary report 200. In an embodiment, the processor 104 receives, or reads, one line of the summary report 200 at a time (hereinafter "a line of the summary report" is referred to as simply a "line"), in sequence, and stores the line in the computer readable storage medium 106 for processing. In other embodiments, the processor 104 reads, stores, and processes the summary report 200 in chunks of lines or in bulk. For the various embodiments, the chip zap module 154 includes the rules, instructions, and algorithms for reading, parsing, storing, and processing the summary report 200. The processor 104 executes the chip zap module 154 to process the summary report 200 data and identify, at least, the date 202, the initial impedance 206, and the delta impedance 210. Based on comparisons with retrieved reference variables, the processor 104 increments counters and determines when to generate an alert. The processing of the data in the summary report 200 is described in more detail in connection with FIG. 3.

Figure 3:
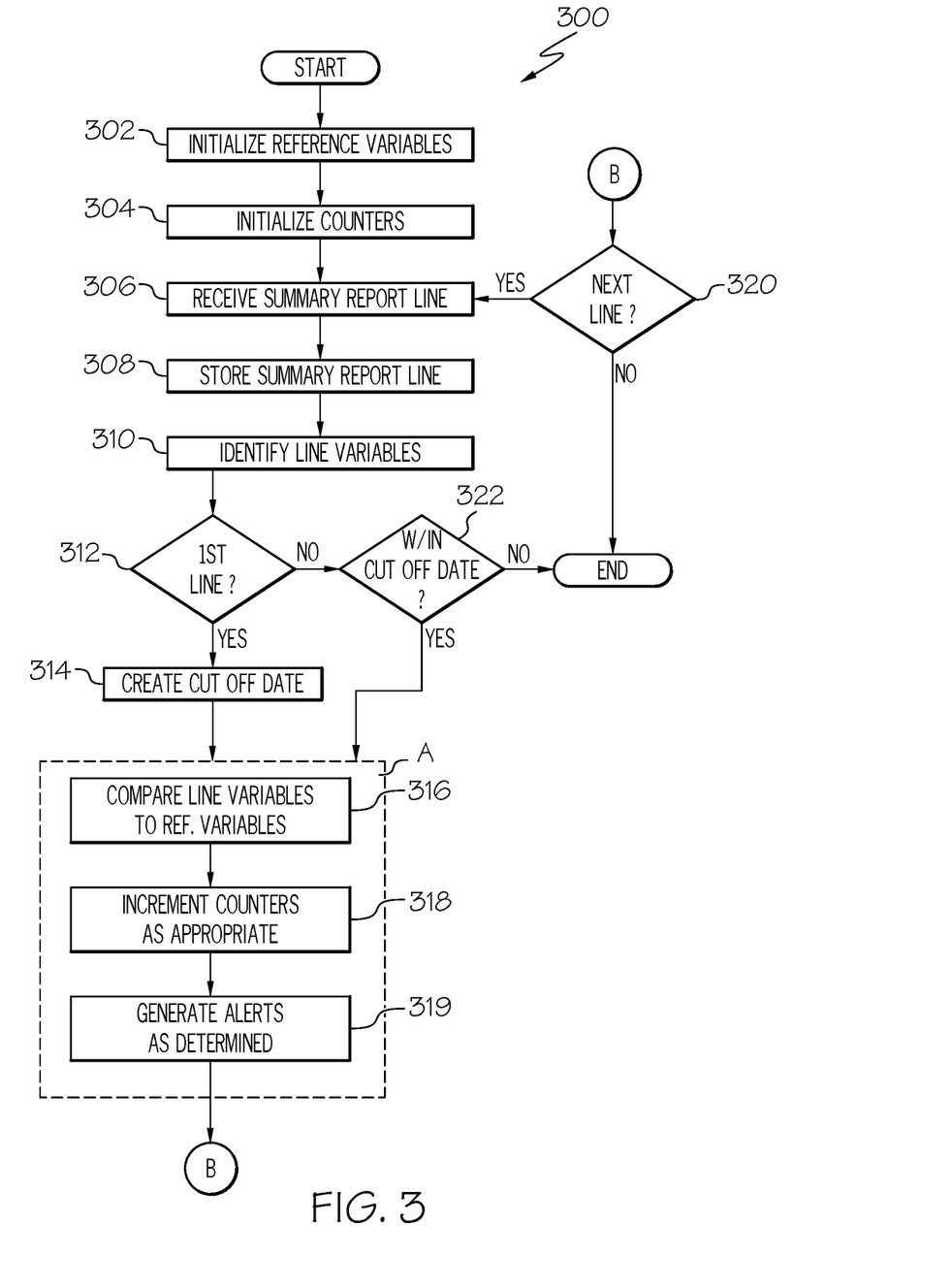
FIGS. 3-4 are flow diagrams of an exemplary method for automatically identifying engine wear based on engine oil debris suitable for use with the system of FIG. 1, in accordance with the exemplary embodiments.
Figure 4:
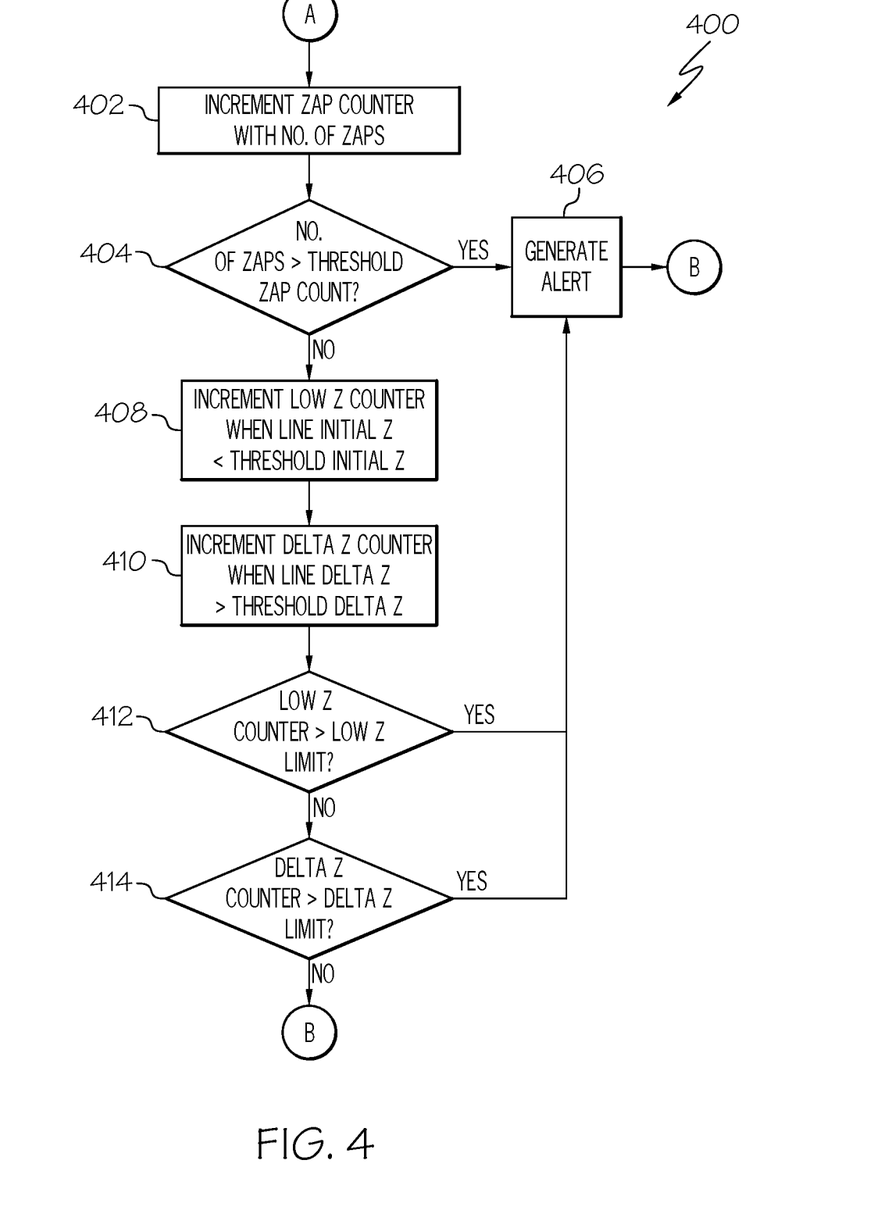

FIG. 3 and FIG. 4 are flow charts for a method 300 for automatically, and without user interaction, monitoring engine wear based on engine oil debris that a system 100 may implement. In the provided embodiment, the computer 102, comprising processor 104 and computer readable storage medium 106, performs method steps. As can be appreciated in light of the disclosure, the order of the method steps is not limited to the sequential execution illustrated in FIGS. 3-4, rather the method steps may be performed in one or more varying orders as applicable, and in accordance with the present disclosure. As can further be appreciated, one or more steps of the method may be added or removed without altering the spirit of the method.

Turning now to FIG. 3, a method 300 for evaluating chip zap data is presented, in accordance with an embodiment. At 302, reference variables are initialized by retrieving the reference variables from the stored values and variables 156. At 304, counters are initialized. Initializing the counters includes setting the zap counter 118 to zero, the low Z impedance counter 120 to zero, and the delta Z counter 122 to zero. At 306, a line of the summary report 200 is received. It is readily appreciated that, if more than one line of the summary report 200 was received by the computer 102, the processor 104 may isolate one line of the summary report 200 for processing then at 306. At 308, the line is stored (in computer readable storage medium 106). At 310, the line is processed to identify line variables comprising a date, an initial impedance, a delta impedance, and a number of zaps. At the time a line is being processed, it may be referred to as the current line. With reference to FIG. 2, the first line 250 date 202 is Oct. 18, 2015, the initial impedance 206 is 232.11, the delta impedance 210 is 1654.12, and the number of zaps 212 is 1.

If, at 312, the current line is the first line of the summary report 200, a cutoff date is created at 314. The created cutoff date may take at least two forms. In an embodiment, the reference delta time comprises an amount of time, and the cutoff date is created by adding the reference delta time to the line date identified in the first line. For example, with reference to FIG. 2, the date of the first line (250) is Oct. 18, 2015, and if the delta time were, for example, forty days, the cutoff date created would be Nov. 28, 2015. In another embodiment, the reference delta time comprises not just an amount of time, but a start date and a stop date (i.e., a specific range of time). In yet another embodiment, the cutoff date may comprise a predetermined and stored range of time; in this scenario, the method step at 314 is not required, and the processor 104 simply initializes the cutoff date prior to using it for processing at 322.

At 316, the identified line variables are compared to the reference variables, at 318 the counters (118, 120, and 122) are incremented as appropriate, and at 319, alerts are generated as determined. The combination of the method steps 316, 318 and 319, indicated by the dotted line box labelled "A," may be expanded into exemplary method steps shown in FIG. 4. If, at 320, there is a next line in the summary report 200, the method 300 returns to 306 for continued summary report 200 processing, and if there is not another line, the method 300 ends. As described earlier, the cutoff date created at 314 is used at 322; if a current line is not the first line in the summary report 200, the identified line date is checked against the previously determined cutoff date at 322. If the line date is within the cutoff date at 322, the method returns to 316 and proceeds as previously described. However, if the identified line date is outside of the cutoff date at 322, the method ends. In the scenario that reference delta time is a specific range of time, processing a line date with a cutoff date at 322 comprises determining whether the line date is within the specific range of time assigned to the cutoff date at 314.

Turning now to FIG. 4, method steps 400, representing the block labeled "A" in FIG. 3, are described. At 402 the zap counter 118 is incremented by the number of zaps in the current line. At 404, if the number of zaps is greater than the threshold zap count, an alert is generated at 406. In an embodiment, the decision at 404 is processed for each line. In another embodiment, the decision at 404 is held off until a plurality of lines in the summary report 200 have been received and processed, the zap counter 118 being incremented for each line of the plurality of lines; in this embodiment, the threshold number of zaps may represent a threshold number of zaps permitted in a range of time, for example by the cutoff date, and the decision at 404 is a comparison of the zap counter number to the threshold number of zaps permitted for the range of time. Generation of an alert at 406 may take a plurality of forms, as described in connection with FIG. 1.

At 408, the low Z counter 120 is incremented when the line initial Z is lower than the threshold initial Z (potentially indicating a metal chip). At 410, the delta Z counter 122 is incremented when the line delta Z is greater than the threshold delta Z. At 412, if the low Z counter is greater than the low Z limit, an alert is generated at 406. Likewise, at 414, if the delta Z counter is greater than the delta Z limit, an alert is generated at 406. In the depicted embodiment, after a single alert is generated at 406, the method 300 determines if there is a next line in the summary report 200. In another embodiment, the method 300 may selectively generate any combination of alerts for each line before moving to the next line. For example, after an alert is generated for the number of zaps at 404, the method may proceed to 412 to determine whether to also generate an alert for the low Z counter and/or may proceed to 414 to determine whether to also generate an alert for the delta Z limit. Stated differently, the method 300 may selectively generate an alert upon the condition, (i) the zap counter reaches the threshold zap count, or (ii) the low Z counter reaches the low Z limit, or (iii) the delta Z counter reaches the delta Z limit. As mentioned, the chip zap module 154 includes program code, rules, and algorithms sufficient for the processor 104 to execute and perform the functions.

The system and method described herein improve upon existing engine health monitoring systems by processing metallic debris data from engine oil to identify engine wear for the engine. The system and method described herein generate alerts based on configurable threshold impedance values. A technical advantage of the improved engine health monitoring system is a reduction of false positives, which increases efficiency and confidence, and reduces cost.

Those of skill in the art will appreciate that the various illustrative functional blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a controller or processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for identifying potential engine wear of an engine based on chip zap data reflecting engine oil debris, the method comprising:

at a processor,
   initializing a threshold zap count as a number of zaps that can be tolerated;
   initializing a zap counter to zero;
   receiving, from an external source, a summary report of the chip zap data, the summary report having one or more lines, each line including: a date, a time, an initial impedance (initial Z), a post-zap impedance, a delta impedance (delta Z), and a number of zaps;
   creating a cutoff date;
   processing a line of the summary report to identify the date, the initial Z, the delta Z, and the number of zaps; and
      incrementing the zap counter by the number of zaps, when the date is within the cutoff date;
   determining whether the zap counter is greater than the threshold zap count; and generating commands to annunciate an alert indicating potential engine wear when the zap counter reaches the threshold zap count.

2. The method of claim 1, further comprising:
comprises
    initializing an impedance value low enough to indicate a metallic object, as a threshold initial Z;
    initializing a number of low impedance entries that may be detected before generating an alert, as a low Z limit;
    initializing a low Z counter to zero;
    incrementing the low Z counter, when the date is within the cutoff date and the initial Z is lower than the threshold initial Z; and
    wherein generating commands for the display device or the audio system to annunciate an alert indicating potential engine wear is
    based upon the occurrence of (i) the zap counter reaches the threshold zap count, or (ii) the low Z counter reaches the low Z limit.

3. The method of claim 2, further comprising:
initializing an impedance value large enough to represent that an object of metallic debris has been cleared, as a threshold delta Z;
initializing a number of lines having large delta Zs that may be tolerated, as a delta Z limit
initializing a delta Z counter to zero;
incrementing the delta Z counter, when the date is within the cutoff date and the delta Z is higher than the threshold delta Z; and
wherein
wherein generating commands for the display device or the audio system to annunciate an alert indicating potential engine wear is
based upon the further occurrence of the delta Z counter reaching the delta Z limit.

4. The method of claim 3, further comprising creating the cutoff date based on a first line date and a variable delta time.

5. The method of claim 4, wherein the line of the summary report is one of a plurality of lines in the summary report, and further comprising:
for each line of the summary report,
    storing the line in a computer readable storage medium;
    processing the line to identify a date, an initial Z, a delta Z, and a number of zaps; and
    when the date is within the cutoff date,
        incrementing the zap counter by the number of zaps;
        incrementing the low Z counter when the initial Z is lower than the threshold initial Z; and
        incrementing the delta Z counter when the delta Z is greater than the threshold delta Z.

6. The method of claim 5, further comprising, at a display system, rendering symbology on a display device responsive to the generated commands to annunciate an alert indicating potential engine wear.

7. The method of claim 5, further comprising, at an audio system, emitting an audible sound responsive to the generated commands to annunciate an alert indicating potential engine wear.

8. The method of claim 5, further comprising generating a file for external transmission responsive to the generated commands to annunciate an alert indicating potential engine wear.

9. The method of claim 8, further comprising:
receiving reference variables via a user input device; and
storing the reference variables in a computer readable storage medium.

10. A system for identifying potential engine wear of an engine based on chip zap data reflecting engine oil debris, the system comprising:
    a processor; and
    a computer readable storage medium coupled to the processor;
    wherein the processor is configured to initialize a threshold zap count as a number of zaps that can be tolerated;
    initialize a zap counter to zero;
    receive, from an external source, a summary report of the chip zap data, the summary report having one or more lines, each line including: a date, a time, an initial impedance (initial Z), a post-zap impedance, a delta impedance (delta Z), and a number of zaps;
    create a cutoff date;
    process a line of the summary report to identify the date, the initial Z, the delta Z, and the number of zaps; and
    increment the zap counter by the number of zaps, when the date is within the cutoff date;
    determine whether the zap counter is greater than the threshold zap count; and
    generate commands to annunciate an alert indicating potential engine wear when the zap counter reaches the threshold zap count.

11. The system of claim 10, wherein the processor is further configured to:
    initialize an impedance value low enough to indicate a metallic object, as a threshold initial Z;
    initialize a number of low impedance entries that may be detected before generating an alert, as a low Z limit;
    initialize a low Z counter to zero;
    increment the low Z counter, when the date is within the cutoff date and the initial Z is lower than the threshold initial Z; and
    wherein the processor is further configured to generate commands for the display device or the audio system to annunciate an alert indicating potential engine wear based upon the occurrence of (i) the zap counter reaches the threshold zap count, or (ii) the low Z counter reaches the low Z limit.

12. The system of claim 11, wherein the processor is further configured to:
    initialize an impedance value large enough to represent that an object of metallic debris has been cleared, as a threshold delta Z;
    initialize a number of lines having large delta Zs that may be tolerated, as a delta Z limit;
    initialize a delta Z counter to zero;
    increment the delta Z counter, when the date is within the cutoff date and the delta Z is higher than the threshold delta Z; and
    wherein the processor is further configured to generate commands for the display device or the audio system to annunciate an alert indicating potential engine wear based upon the further occurrence of the delta Z counter reaching the delta Z limit.

13. The system of claim 12, wherein the line of the summary report is one of a plurality of lines in the summary report, and wherein the processor is further configured to:
    for each line of the summary report,
        store the line in the computer readable storage medium;
        process the line to identify a date, an initial Z, a delta Z, and a number of zaps; and
        when the date is within the cutoff date,
            increment the zap counter by the number of zaps;
            increment the low Z counter when the initial Z is lower than the threshold initial Z; and increment the delta Z counter when the delta Z is greater than the threshold delta Z.

14. The system of claim 13, wherein the processor is further configured to generate commands for the alert in a soft file for external transmission.

15. The system of claim 14, further comprising a display system configured to render symbology on a display device responsive to the generated commands to annunciate an alert indicating potential engine wear.

16. The system of claim 15, further comprising an audio system configured to emit sounds responsive to the generated commands to annunciate an alert indicating potential engine wear.

* * * * *